United States Patent [19]

Jacquet et al.

[11] 4,381,919
[45] May 3, 1983

[54] HAIR DYE COMPOSITION CONTAINING QUATERNIZED POLYMERS

[75] Inventors: Bernard Jacquet, Antony; Gérard Lang, Epinay-sur-Seine, both of France

[73] Assignee: Societe Anonyme dite: L'Oreal, Paris, France

[21] Appl. No.: 101,562

[22] Filed: Dec. 10, 1979

Related U.S. Application Data

[63] Continuation-in-part of Ser. No. 899,467, Apr. 24, 1978, Pat. No. 4,197,865, which is a continuation of Ser. No. 702,924, Jul. 6, 1976, abandoned.

[30] Foreign Application Priority Data

Jul. 4, 1975 [LU]  Luxembourg ............................ 72901
Nov. 13, 1975 [LU]  Luxembourg ............................ 73792

[51] Int. Cl.³ .............................................. D06D 5/00
[52] U.S. Cl. .......................................... 8/405; 8/406; 8/407; 8/408; 8/411; 8/412; 32/7; 424/47; 424/59; 424/63; 424/70; 424/78; 424/358; 564/194
[58] Field of Search .................. 8/405, 406, 407, 408, 8/411, 412

[56] References Cited

U.S. PATENT DOCUMENTS

| | | | |
|---|---|---|---|
| 2,271,378 | 1/1942 | Searle .............................. | 424/329 |
| 3,592,581 | 7/1971 | Shansky et al. ................. | 8/405 |
| 3,761,418 | 9/1973 | Parran, Jr. ....................... | 252/106 |
| 3,769,398 | 10/1973 | Hewitt ............................. | 424/325 |
| 3,778,476 | 12/1973 | Rembaum et al. ............... | 525/540 |
| 3,817,698 | 6/1974 | Kalopissis et al. .............. | 8/405 |
| 3,849,548 | 11/1974 | Grand .............................. | 424/70 |
| 3,874,870 | 4/1975 | Green et al. ..................... | 424/78 |
| 3,912,808 | 10/1975 | Sokol ............................... | 8/405 |
| 3,923,973 | 12/1975 | Green et al. ..................... | 424/78 |
| 3,929,990 | 12/1975 | Green et al. ..................... | 424/78 |
| 3,961,042 | 6/1976 | Green et al. ..................... | 424/78 |
| 3,966,904 | 6/1976 | Green et al. ..................... | 424/78 |
| 4,213,960 | 7/1980 | Grollier et al. .................. | 8/405 |
| 4,217,914 | 8/1980 | Jacquet et al. .................. | 424/78 |
| 4,240,450 | 12/1980 | Grollier et al. .................. | 8/406 |

*Primary Examiner*—Dale R. Ore
*Attorney, Agent, or Firm*—Cushman, Darby & Cushman

[57] ABSTRACT

A quaternized polymer having recurring units of the formula

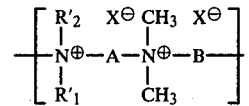

wherein
$X^{\ominus}$ represents an anion derived from an organic or mineral acid;
$R'_2$ is an aliphatic radical having a maximum of 20 carbon atoms;
$R'_1$ is an alphatic, alicyclic or arylaliphatic radical containing a minimum of 2 carbon atoms and a maximum of 20 carbon atoms, or $R'_1$ and $R'_2$ together with the nitrogen atom to which they are attached form a ring capable of containing a second heteroatom other than said nitrogen;
A represents a divalent group of the formula

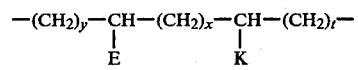

wherein, x, y and t are whole numbers ranging from 0 to 11 and being such that the sum (x+y+t) is greater than or equal to 0 and less than 18, and E and K represent hydrogen or an aliphatic radical having less than 18 carbon atoms;
B represents a divalent group of the formula

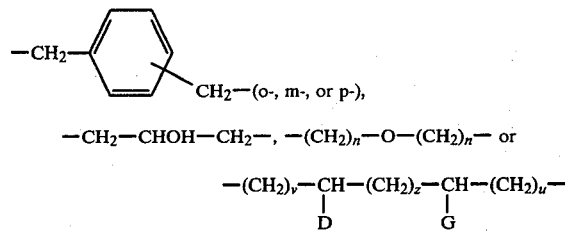

$-CH_2-CHOH-CH_2-$, $-(CH_2)_n-O-(CH_2)_n-$ or $$-(CH_2)_v-\underset{D}{CH}-(CH_2)_z-\underset{G}{CH}-(CH_2)_u-$$

wherein D and G represent hydrogen or an aliphatic radical having less than 18 carbon atoms and v, z, and u are whole numbers ranging from 0 to 11, two of them being able to be simultaneously equal to 0 such that the sum (v+z+u) is greater than or equal to 1 and lower than 18, and such that the sum (v+z+u) is greater than 1 when the sum (x+y+t) is equal to 0, and n is a whole number equal to 2 or 3.

The polymers are usefully employed in cosmetic compositions for application to the hair or skin.

17 Claims, No Drawings

HAIR DYE COMPOSITION CONTAINING QUATERNIZED POLYMERS

This application is a continuation-in-part of our application Ser. No. 899,467, filed Apr. 24, 1978, now U.S. Pat. No. 4,197,865, which, in turn, is a continuation of our application Ser. No. 702,924, filed July 6, 1976, now abandoned.

The present invention relates to new polymers possessing quaternary ammonium groups, as well as to a process for preparing them and to their use as cosmetic agents.

The invention is more particularly directed to quaternized polymers having recurring units of the formula:

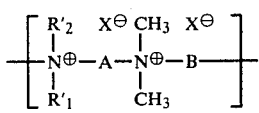
(I)

wherein $X^\ominus$ represents an anion derived from an organic or mineral acid;

$R'_2$ is an aliphatic radical containing a maximum of 20 carbon atoms;

$R'_1$ is an aliphatic, alicyclic or arylaliphatic radical containing a maximum of 20 and a minimum of 2 carbon atoms; or $R'_1$ and $R'_2$ together with nitrogen atom to which they are attached form a ring capable of containing a second heteroatom other than nitrogen;

A represents a divalent group of the formula

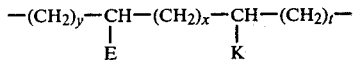

wherein x, y and t are whole numbers ranging from 0 to 11 and such that the sum (x+y+t) is greater than or equal to 0 and lower than 18, and E and K represent hydrogen or an aliphatic radical having less than 18 carbon atoms; and B represents a divalent group of the formula

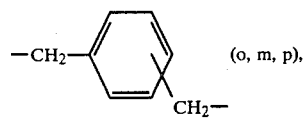
(o, m, p), $-CH_2-CHOH-CH_2-$, $-(CH_2)_n-O-(CH_2)_n-$, or

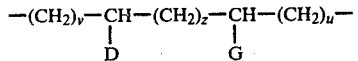

wherein D and G represent hydrogen or an aliphatic radical having less than 18 carbon atoms and v, z and u are whole numbers ranging from 0 to 11, two of them being able to be simultaneously equal to 0 and such that the sum (v+z+u) is greater than or equal to 1 and lower than 18 and such that the sum (v+z+u) is greater than 1 when the sum (x+y+t) is equal to 0, and n is a whole number equal to 2 or 3.

In that which follows, the expression "polymer of formula I" means those having the recurring units as defined above.

The terminal groups of the polymers of formula I vary principally with the amounts of the initial reactants. They can thus be of the type

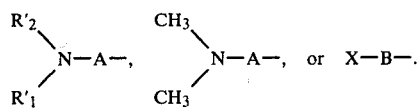

In formula I, $X^\ominus$ represents principally a halide anion such as bromide, iodide or chloride, or an anion derived from other mineral acids such as phosphoric acid or sulfuric acid, or the like, or even an anion derived from an organic sulfonic or carboxylic acid, generally an alkanoic acid having from 2 to 12 carbon atoms, for example, acetic acid; a phenylalkanoic acid, for example, phenylacetic acid; benzoic acid; lactic acid; citric acid; or paratoluene sulfonic acid. When $R'_1$ represents an aliphatic radical, it is a question principally of an alkyl or a cycloalkyl radical wherein the alkyl has less than 20 carbon atoms, i.e. 1 to 19 carbon atoms, preferably not more than 18 carbon atoms and more preferably not more than 16 carbon atoms. When $R'_1$ represents an alicyclic radical, it is a question generally of a cycloalkyl radical having 5 or 6 chains. When $R'_1$ represents an arylaliphatic radical, it is a question generally of an aralkyl radical such as a phenylalkyl wherein the alkyl moiety has, preferably, from 1 to 3 carbon atoms. When the substituent E, K, D or G is an aliphatic radical, it is a question generally of an alkyl radical having from 1 to 17 carbon atoms and preferably from 1 to 12 carbon atoms. Preferably v, z and u represent numbers ranging from 1 to 5, two of them being able besides to be equal to 0; x, y and t are preferably numbers ranging from 0 to 5. When B represents xylylene, it can be an o, m- or, preferably, p-xylylene.

Representative polymers of formula I include principally those for which: $R'_1$ is alkyl having from 2 to 18 carbon atoms and preferably 2 to 16 carbon atoms, a benzyl radical or a cyclohexyl radical; $R'_2$ is an alkyl radical having from 1 to 20 carbon atoms, and preferably 1 to 8 carbon atoms or the $R'_1$ and $R'_2$ together represent a polymethylene radical having preferably 4 or 5 carbon atoms and the ring formed by $R'_1$ and $R'_2$ can carry as a second heteroatom oxygen or sulfur; in particular $R'_1$ and $R'_2$ together can represent the divalent radical $-(CH_2)_2-O-(CH_2)_2-$; A is a polymethylene radical having from 2 to 12 and preferably 3 to 10 carbon atoms which can optionally be branched by one or two alkyl substituents having from 1 to 12 carbon atoms, B is xylylene, or B is a polymethylene radical having from 3 to 10, preferably 3 to 6 carbon atoms, which can optionally be branched by one or two alkyl substituents having from 1 to 12 carbon atoms; and X is an atom of chlorine, iodine or bromine.

Typical of these latter polymers of formula I include, in particular, those for which $R'_1$ is ethyl, propyl, butyl, hexyl, octyl, decyl, dodecyl, hexadecyl, cyclohexyl or benzyl; A is a polymethylene radical having 3, 5, 6, 8, 9 or 10 carbon atoms, optionally branched by one or two alkyl substituents having from 1 to 12 carbon atoms; and B is o- or p-xylylene, or B is a polymethylene radical having 3, 4, 5 or 6 carbon atoms, optionally branched by one or two alkyl substituents having from 1 to 12 carbon atoms.

The invention relates principally to the polymers of formula I described hereinafter in Examples 1–31.

The present invention includes, of course, polymers of formula I wherein A, B, R'$_1$ or R'$_2$ have several different values in the same polymer chain. Such polymers can be obtained in accordance with the description of the process for preparing the polymers of formula I given below.

The invention also relates to a process for preparing the polymers of formula I which comprises:

(a) polycondensing a ditertiary diamine of the formula $$\begin{array}{c} R'_2 \quad CH_3 \\ | \quad\quad | \\ N-A-N \\ | \quad\quad | \\ R'_1 \quad CH_3 \end{array}$$

and a dihalide of the formula X—B—X, wherein A, B, R'$_1$, R'$_2$ and X have the meanings given above; or (b) polycondensing a ditertiary diamine of the formula $$\begin{array}{c} R'_2 \quad CH_3 \\ | \quad\quad | \\ N-B-N \\ | \quad\quad | \\ R'_1 \quad CH_3 \end{array}$$

and a dihalide of the formula X—A—X.

The polycondensation reactions according to methods (a) or (b) above can be carried out in a solvent or in a mixture of solvents favoring quaternization reactions. Such solvents include water, dimethyl formamide, acetonitrile, lower alcohols, principally lower alkanols such as methanol and the like.

The reaction temperature can vary between 10° and 150° C. and preferably between 20° and 100° C.

The duration of the reaction can depend upon such easily determined factors as the nature of the solvent, the initial reactants and the degree of polymerization desired.

Generally the initial reactants are reacted in equimolar quantities, but it is possible to use either the diamine or the dihalide in a slight excess, this excess being lower than 20 molar percent.

It is possible to regulate the average length of the chain by adding at the start of the reaction or during the course thereof, a small quantity (1 to 15 mole percent relative to one of the initial reactants) of a monofunctional reactant such as a tertiary amine or a monohalide. In this case, at least a portion of the terminal groups of polymer I obtained is constituted either by the tertiary amine group used, or by the hydrocarbon group of the monohalide. The polymers of formula I having such terminal groups also within the scope of the present invention.

There can also be employed as the initial reactant, either a mixture of ditertiary diamines, or a mixture of dihalides, or even a mixture of ditertiary diamines and a mixture of dihalides with the proviso that the ratio of the total molar quantities of diamines and dihalides is near 1.

The ditertiary diamines used as the initial reactant in the above process are known or can be prepared using known methods.

For example, diamines of the formula:

$$\begin{array}{c} R'_2 \quad\quad\quad\quad CH_3 \\ \backslash \quad\quad\quad\quad\quad / \\ N-(CH_2)_n-N \\ / \quad\quad\quad\quad\quad \backslash \\ R'_1 \quad\quad\quad\quad CH_3 \end{array}$$

wherein n=3 can be obtained by cyanoethylation of secondary amines of the formula $$\begin{array}{c} R'_2 \\ \backslash \\ NH \\ / \\ R'_1 \end{array}$$

in accordance with Whitmore et al JACS, 66, p. 725 (1944), reduction of the propionitrile amine and methylation by the method of Eschweiler-Clarke using a formaldehyde-formic acid mixture (cf. Chem. Ber. 38, p. 880 (1905) and JACS, 55, p. 4571 (1933).

The other diamines used in the present invention can be prepared by methylation, according to the method described above, of diamines having the formulas $$\begin{array}{c} R'_1 \\ \backslash \\ N-A-NH_2 \\ / \\ R'_2 \end{array} \quad \text{or} \quad \begin{array}{c} H \\ \backslash \\ N-A-NH_2 \\ / \\ R'_1 \end{array}$$

which in turn can be obtained by a method derived from that described by H. E. Franck et al, JACS, 67, p. 882 (1945) or even a method analogous to the method described in U.S. Pat. No. 3,234,139.

Although the invention is not limited to polymers of formula I whose degree of polymerization is necessarily limited, the polymers of formula I generally have a molecular weight ranging between 5,000 and 50,000. Further the polymers of formula I are generally soluble in at least one of three solvents comprising water, ethanol or a water-ethanol mixture. Evaporation of the solvent from a solution of the polymer yields films which generally exhibit good affinity for keratinic fibers.

The polymers of the present invention exhibit interesting cosmetic properties when they are introduced into cosmetic compositions to be applied to the hair or the skin. Thus the present invention also relates to the polymers of formula I as cosmetic agents.

The present invention also relates to cosmetic compositions comprising at least one polymer of formula I. These cosmetic compositions include generally at least one adjuvant conventionally employed in cosmetic compositions. Further the polymer of formula I can be present in these composition either as the principal active component, or as an additive.

The cosmetic compositions of the present invention can be provided in the form of an aqueous, alcoholic or hydroalcoholic solution, the alcohol being principally a lower alkanol such as ethanol or isopropanol, or in the form of creams, gels, emulsions, or even in the form of an aerosol which also contains a suitable propellant.

The adjuvants generally present in the cosmetic compositions of this invention include, for example, perfumes, dyes, preservatives, sequestering agents, thickening agents and the like.

Furthermore, the cosmetic compositions of the present invention are those which are ready for use, as well as those in concentrated form which are generally diluted before use. Thus, the cosmetic compositions of the present invention need not be limited to any particular concentration of the polymer of formula I.

Generally, however, the concentration of the polymer of formula I in the cosmetic compositions of this invention ranges between 0.25 and 10 weight percent and preferably between 0.5 and 5 weight percent.

The polymers of formula I exhibit interesting cosmetic properties when they are applied to the hair, either alone or with other active substances in such treatments as shampooing, dyeing, hair setting and the like. When so used, these polymers significantly improve the qualities of the hair.

For example, the polymers assist and facilitate the treatment of untangling wet hair. Even when present in high concentration, they do not impart to wet hair a sticky feeling or appearance.

Contrary to conventional cationic agents, the polymers of this invention do not render dry hair heavy, and they facilitate then bouffant hair styles. The polymers of this invention also impart to dry hair lively characteristics and a shiny appearance.

The said polymers also contribute effectively to the elimination of disadvantages associated with hair sensitized by such treatments as bleaching, permanent waving or dyeing. It is known that sensitized hair is often dry, dull and rough, and difficult to comb and to style.

The polymers of the present invention also exhibit, in particular, great usefulness when they are employed as pretreating agents, notably before an anionic and/or non-ionic shampooing, or before oxidation dyeing, followed by an anionic and/or non-ionic shampooing. When so employed, the thus treated hair is particularly easy to comb and has a very soft feel.

The polymers of this invention are also useful as pretreating agents for other hair treatments such as permanent wave treatments.

The polymers of formula I are useful in cosmetic compositions for the hair in accordance with the invention either as an additive, or as the principal active component, in hair setting lotions, hair treating lotions, styling creams or gels, or even as an additive in shampoo compositions, hair setting compositions, permanent waving compositions, hair dyeing compositions, hair restructuring compositions, anti-dandruff lotions or hair lacquer compositions.

The cosmetic compositions for the hair can be principally:

(a) hair treating compositions comprising as the active component, at least one polymer of formula I in an aqueous or hydroalcoholic solution. These compositions can be provided in spray containers, principally in aerosol containers.

The pH of these lotions is near neutral and can range for example from 6 to 8. If necessary, the pH can be adjusted to the desired value, by adding either an acid such as citric acid, or a base, principally an alkanol amine such as monoethanolamine or triethanolamine.

To treat the hair with such a composition, the same is applied to wet hair and is permitted to remain in contact therewith for 3–15 minutes. Thereafter, the hair is rinsed.

Also, if desired, the hair can be set in a conventional manner.

(b) shampoo compositions comprising at least one polymer of formula I and a cationic, anionic, non-ionic or amphoteric detergent in an amount between 0.5 to 55 weight percent.

The cationic detergents are principally long chain quaternary ammoniums, esters of fatty acids and amino alcohols, or polyether amines.

The non-ionic detergents are principally esters of polyols and sugars, the condensation products of ethylene oxide on fatty bodies, on long chain alkyl phenols, on long chain mercaptans or on long chain amides, and polyhydroxylated polyethers of fatty alcohol and polyglycerolated fatty alcohols.

These shampoo compositions can also include various adjuvants such as, for example, perfumes, dyes, preservatives, thickening agents, foam stabilizers, softening agents, or even one or more cosmetic resins. When the dye employed is an oxidation dye, the composition can be provided in two parts which are then mixed at the moment of use. One of the parts contains the dye and the other part contains an oxidizing agent such as hydrogen peroxide.

(c) hair setting lotions, principally for sensitized hair, comprising at least one polymer of formula I in an aqueous, alcoholic or hydroalcoholic solution.

They can also contain one or more other cosmetic resins, principally vinyl homopolymers or copolymers as, for example, polyvinylpyrrolidone, copolymers of vinylpyrrolidone and vinyl acetate, copolymers of crotonic acid and vinyl acetate and the like.

The pH of these hair setting lotions can range generally between 4.5 and 7.5. The pH, if desired, can be modified, for example, by the addition of an alkanolamine such as monoethanolamine or triethanolamine.

(d) hair dye compositions comprising at least one polymer of formula I, a hair dye and a carrier.

The carrier is preferably selected so that the composition is in the form of a powder, a cream or a gel.

When the dye employed is an oxidation dye, the dye composition can be packaged in two parts, one part preferably in powder form containing the dye, the other part containing the oxidizing agent such as $H_2O_2$. Both parts are mixed together at the moment of use.

It is appropriate to state that in the present invention, the hair dye compositions also include hair bleaching composition. In this latter instance, the coloring agent is replaced by an oxidizing agent, such as hydrogen peroxide.

It is known that in the actual technique of dyeing or bleaching hair, a dye or bleaching vehicle is used so as to provide the composition either in the form of a cream or in the form of a gel or a liquid gelable by dilution.

Generally, creams are obtained either starting with soaps of $C_{12}$ to $C_{20}$ fatty acids, or starting with fatty alcohols in the presence of anionic or non-ionic emulsifiers.

The soaps can be prepared using, as an initial reactant a natural or synthetic fatty acid having from 12 to 20 carbon atoms such as lauric acid, myristic acid, palmitic acid, oleic acid, stearic acid, hydroxystearic acid, arachic acid, ricinoleic acid, lanolinic acid, phenylstearic acid, linoleic acid, at a concentration between 1 and 60 weight percent and preferably between 5 and 30 weight percent (before dilution).

The alkalizing agent used with the above fatty acid to form the soap can be principally NaOH, KOH, ammonia, monoethanolamine, diethanolamine, triethanolamine, mono and diisopropanolamine, N-ethyl morpholine, 2-amino 1-butanol, 2-amino-2-methyl 1-propanol or a mixture thereof.

The creams can also be formulated starting with natural or synthetic alcohols having between 12 and 20 carbon atoms in admixture with the emulsifiers.

Representative fatty alcohols include, in particular, alcohols derived from the fatty acids of copra, myristyl alcohol, cetyl alcohol, stearyl alcohol, arachidyl alcohol, isostearyl alcohol, hydroxystearyl alcohol, oleyl alcohol and ricinoleyl alcohol, in an amount ranging generally between 1 and 60 weight percent and preferably between 5 and 30 percent by weight.

The emulsifiers useful in compositions in the form of a cream can be $C_{10}$–$C_{20}$ natural or synthetic fatty alcohols oxyethylenated or polyglycerolated, as for example, polyoxyethylenated oleyl alcohol having 10–30 moles of ethylene oxide, oxyethylenated cetyl alcohol having 6 to 10 moles of ethylene oxide, cetylstearyl alcohol oxyethylenated with 10 moles of ethylene oxide, oleocetyl alcohol oxyethylenated with 30 moles of ethylene oxide, stearyl alcohol oxyethylenated with 10, 15 or 20 moles of ethylene oxide, oleyl alcohol polyglycerolated with 4 moles of glycerol and synthetic fatty alcohols having between 9 and 20 carbon atoms and being polyoxyethylenated with 5 to 30 moles of ethylene oxide.

These non-ionic emulsifiers are present in amounts generally between 1 and 60 percent and preferably between 5 and 30 percent by weight.

Other emulsifiers which can be used include alkyl sulfates oxyethylenated or not, such as sodium lauryl sulfate, ammonium lauryl sulfate, sodium cetylstearyl sulfate, triethanolamine cetylstearyl sulfate, monoethanolamine or triethanolamine lauryl sulfate, sodium lauryl ether sulfate oxyethylenated with, for example, 2.2 moles of ethylene oxide, monoethanolamine lauryl ether sulfate oxyethylenated with, for example, 2.2 moles of ethylene oxide.

These components are present in amounts generally between 1 and 60 percent and preferably between 3 and 15 percent by weight.

Further, these creams can contain various conventional adjuvants such as fatty amides.

Representative fatty amides include, preferably, mono- or di-ethanolamides, and amides of the acids derived from copra and from lauric acid or from oleic acid, in an amount ranging generally between 0 and 15 weight percent.

These compositions can also contain sequestering agents such as ethylene diamine tetracetic acid or its salts, thickening agents, perfumes and the like.

In accordance with a particularly interesting embodiment of the present invention, the hair dyeing compositions are provided in the form of a gelable liquid. The gelable liquid provides, principally, the advantage of being more easy to handle and to prepare than creams, principally in view of producing a mixture with hydrogen peroxide. Moreover, the transparency of the gels permit to follow without difficulty the development of the coloration of the hair.

It is known that gelable liquids can be obtained principally by using as an initial reactant a non-ionic which is slightly oxyethylenated or polyglycerolated and solvents.

The polymers of the present invention exhibit principally the advantage of being compatible with such non-ionic compounds conventionally used for the preparation of gelable liquids.

Representative oxyethylenated non-ionic compounds include natural or synthetic liquid fatty alcohols such as oleyl alcohol having 4 and 10 moles of ethylene oxide, $C_{10}$–$C_{12}$ synthetic fatty alcohol having 4 and 6 moles of ethylene oxide, $C_9$–$C_{15}$ synthetic fatty alcohol having 2, 6 and 9 moles of ethylene oxide, nonylphenol polyether having 4 moles of ethylene oxide and nonylphenol polyether having 9 moles of ethylene oxide.

Representative polyglycerolated non-ionic compounds include, in particular, oleyl alcohol having 2 moles of glycerol and oleyl alcohol glycerolated with 4 moles of glycerol.

These components are present in amounts generally between 5 and 60 weight percent and preferably between 5 and 40 weight percent.

The solvents used can be lower aliphatic alcohols such as ethyl alcohol, propyl or isopropyl alcohol, glycols such as propylene glycol, methyl glycol, ethyl glycol, diethylene glycol, dipropylene glycol, hexylene glycol, diethylene glycol monoethyl ether or ethylene glycol mono butyl ether.

These solvents, or mixtures thereof, are generally used in amounts (before dilution) of 2 to 20 percent and preferably from 5 to 15 weight percent.

The gelable composition can also contain various conventional adjuvants. These adjuvants can be fatty amides, natural or synthetic fatty alcohols, alkaline alkyl sulfates oxyethylenated or not, preservatives, sequestering agents and perfumes.

Representative fatty amides include, in particular, oleic or lauric diethanolamide and copra mono- or di-ethanolamide. These amides are generally used in amounts (before dilution) of 0.5 to 15 percent and preferably from 1 to 10 percent by weight.

Representative natural or synthetic fatty alcohols include, in particular, oleyl alcohol, lauryl alcohol, octyldodecyl alcohol, hexyldodecyl alcohol, isostearyl alcohol, ricinoleyl alcohol and linoleyl alcohol. These alcohols are generally used in amounts (before dilution) of 1 to 25 percent and preferably from 5 to 15 percent by weight.

Representative alkaline alkyl sulfates, oxyethylenated or not, include, in particular, sodium lauryl sulfate, ammonium or triethanolamine lauryl sulfate, monoethanolamine lauryl sulfate, oxyethylenated sodium laurylether sulfate having, for example, 2.2 moles of ethylene oxide and oxyethylenated monoethanolamine laurylether sulfate having, for example, 2.2 moles of ethylene oxide.

These sulfates are generally employed in amounts (before dilution) of 0.5 to 15 percent and preferably from 1 to 10 percent by weight.

When admixed with hydrogen peroxide, in dilution amounts most often used, i.e. from 1 to 3 times, so as to have in the resulting admixture a sufficient amount of hydrogen peroxide and ammonia to obtain a lightening of the hair color, the dye or bleaching vehicles in the form of a cream, produce a cream and the supports in the form of gelable liquids yield a gel.

The present invention also relates to a hair dye composition which contains the dye support or vehicle of this invention in admixture with direct or oxidation dyes.

The present invention further relates to hair dye or bleaching compositions provided in two parts to be mixed together at the time of use, the first part comprising the vehicle, containing optionally an oxidation dye, and the second part comprising an oxidizing agent, such as hydrogen peroxide. These two parts are combined in a package permitting their method of use.

It is known that oxidation dyes are aromatic compounds of the diamine type, aminophenols, or phenols. Such compounds are generally not dyes, per se, but are transformed into dyes by condensation in the presence of an oxidizing medium comprising, generally, hydrogen peroxide. Representative oxidation dyes include, on the one hand, bases which are para or ortho derivatives selected from diamines and aminophenols and, on the other hand, compounds termed modifiers or couplers which are meta derivatives selected from the meta-diamines, meta-aminophenols and polyphenols.

Other dyes useful in the present invention include direct dyes such as nitrated dyes, anthraquinone derivatives, triphenylmethane dyes, azo dyes, metalliferous dyes, xanthenic dyes, acridinic dyes and the like.

Generally, the hair dye support or vehicle of the present invention contains from 0.5 to 10 percent by weight and, preferably, from 1 to 3 percent by weight of quaternized polymers such as those defined above.

The pH of the hair dye or bleach support of the present invention is generally between 6 and 11 and preferably between 8 and 11, and it is obtained by the addition, if necessary, of an appropriate basic agent, or of an acidic agent such as tartaric acid, citric acid, acetic acid, hydrochloric acid, phosphoric acid and the like.

Preferably, the compositions of the present invention are free from anionic polymers.

The present invention also relates to a hair dyeing or bleaching process comprising, principally, applying to the hair a hair dye or bleaching support or vehicle such as defined above, containing, optionally, one or more hair dyes, and admixed optionally with an oxidizing agent such as hydrogen peroxide, permitting said support or vehicle to remain in contact with the hair for a time sufficient to obtain the desired dyeing or bleaching effect, and thereafter rinsing the hair.

Generally, the composition is permitted to remain in contact with the hair for 5 to 45 minutes, and preferably for 15 to 30 minutes.

The amount of hair dye or bleaching composition applied to the hair is generally between about 10 to 100 grams.

(e) hair lacquers comprising an alcoholic or hydroalcoholic solution of a conventional hair lacquer cosmetic resin and at least one polymer of formula I, the resulting composition being packaged under pressure in an aerosol container and admixed with an aerosol propellant.

For example, an aerosol lacquer according to the present invention can be provided by adding a conventional cosmetic resin and the polymer of formula I to a mixture of an anhydrous aliphatic alcohol such as ethanol or isopropanol and of a propellant or a mixture of liquified propellants, such as halogenated hydrocarbons, including trichlorofluoromethane or dichlorodifluoromethane.

However, it is possible to add to the hair lacquers in accordance with the present invention such adjuvants as dyes, plasticizers or any other conventional adjuvant;

(f) hair restructuring lotions comprising at least one agent having the capability of restructuring the hair and at least one polymer of formula I.

Hair restructuring agents useful in such lotions are, for example, methylol derivatives described in French Pat. Nos. 1,519,979; 1,519,980; 1,519,981; 1,519,982 and 1,527,085;

(g) hair pretreatment compositions which can be provided principally in the form of an aqueous or hydroalcoholic solution, optionally packaged in an aerosol container, or in the form of a cream or gel. These pretreatment compositions can be applied to the hair before shampooing, generally before an anionic and/or a non-ionic shampooing; before an oxidation dyeing followed by an anionic and/or non-ionic shampooing; or even before a permanent waving operation.

In these pretreatment compositions, the polymer of formula I comprises the active component, and its concentration ranges generally from 0.25 to 10%, and particularly from 0.5 to 5%, by weight, of the composition. The pH of these compositions ranges generally between about 3 and 9.

The pretreatment compositions can contain various adjuvants, for example, resins conventionally employed in cosmetic compositions for the hair; pH modifiers, for example amino alcohols such as monoethanolamine, and the like, as well as those other adjuvants indicated for the compositions described in paragraph (a) above.

(h) Compositions for use in permanently waving or stretching the hair.

It is known that the classic technique for effecting the permanent deformation of hair comprises, in a first stage, opening the S—S bond of the keratin of the hair using a composition containing a reducing agent and then, after having, preferably, rinsed the hair, reforming in a second stage the said S—S bond by applying to the hair, which is eventually extended, an oxidizing composition, so as to impart to the hair the desired configuration.

The formulation of the said reducing and oxidizing compositions is also known and is described in various cosmetology publications. Notable among these publications is that of E. Sidi and C. Zviak, Problémes Capillaires, Paris, 1966 (Gauthier-Villard).

The permanent compositions of the present application are, preferably, reducing compositions for effecting the first stage in the method of permanently waving or stretching the hair.

These compositions contain, in addition to the reducing agent, adjuvants which permit them to be provided in the form of lotions, or in the form of a powder to be diluted with water.

The reducing agent is, most often, a mercaptan such as, for example, thioglycerol or even thioglycolic acid or a derivative thereof.

The compositions most frequently used are based on thioglycolic acid, or a derivative thereof, principally a salt such as an ammonium, morpholino or ethylamine salt; an ester such as a glycol or glycerol ester; a hydrazide or an amide.

The amount of the reducing agent employed is that required to obtain the reduction of a sufficient number of S—S bonds. This amount has heretofore been studied and determined and is described in cosmetogoly publications. For example, when thioglycolic acid is employed it is used generally in an amount in the order of about 1 to 11 weight percent.

The pH of these reducing compositions which are employed in the first stage of a permanent operation generally ranges from 7 to 11.

The reducing compositions of the present invention contain, preferably, from 0.25 to 10 percent by weight of the polymer of formula I, and more preferably from 0.5 to 5 weight percent.

These reducing lotions for use in the first stage of the permanent operation are most often aqueous solutions capable of also containing pH modifiers (for example ammonia, ammonium carbonate or bicarbonate), auxiliary reducing agents such as sulfites (for example, sodium or potassium sulfites), solvents such as ethanol or isopropanol, ionic or cationic surfactants, perfumes and/or dyes.

The polymers of formula I are compatible with the components and adjuvants used in the permanent waving or hair dyeing compositions of the present invention.

The present invention thus also relates to a process for permanently waving or stretching the hair, comprising applying to the hair a sufficient amount of a reducing composition such as defined above, permitting said composition to remain in contact with the hair for about 5 to 30 minutes, rinsing the hair and thereafter applying to the hair an oxidizing composition in an amount sufficient to reform the S—S bonds of the keratin of the hair.

The oxidizing agent is, preferably, $H_2O_2$, a persalt such as sodium perborate or sodium persulfate, sodium, calcium or magnesium bromate, sodium iodate or the like.

The extension of the hair is generally carried out by rolling the hair on curlers for the permanent waving or by combing the hair for the permanent stretching. In the permanent waving, the hair rolling is effected preferably after application of the reducing composition to the hair.

After application of the oxidizing composition to the hair and contact thereof with the hair for a sufficient time, the extension of the hair is discontinued by, for instance, unrolling the hair from the curlers. Thereafter, the hair is rinsed and set.

The polymers of the present invention also exhibit interesting cosmetic properties when they are applied to the skin.

Principally, they impart to the skin a significant softness to the touch. These properties then make the polymers of the present invention useful in formulating cosmetic compositions for the skin. Moreover, these compositions for the skin generally include at least one adjuvant conventionally employed in such cosmetic compositions for the skin and can be provided, for example, in the form of creams, gels, emulsions or as aqueous, alcoholic or hydroalcoholic solutions and the like.

The adjuvants generally present in these cosmetic compositions are, for example, perfumes, dyes, preservatives, sequesterants, emulsifiers, thickening agents and the like.

These compositions for the skin constitute principally treating creams or lotions for the face and hands, antisolar creams, tinting or shading creams, makeup remover milks, bath oils or bubble bath formulations. They can also be employed in deodorants. Such compositions can be prepared in accordance with conventional procedures.

For example, to obtain a cream, an aqueous phase containing the polymer in solution and optionally other components or adjuvants is emulsified with an oil phase.

The oil phase can comprise various products such as paraffin oil, vaseline oil, sweet almond oil, avocado oil, olive oil, esters of fatty acids such as glyceryl monostearate, ethyl or isopropyl palmitate, alkyl myristates such as propyl, butyl or cetyl myristate. Also fatty alcohols such as cetyl alcohol or waxes such as beeswax can be included in such compositions.

The polymers of this invention can be provided in cosmetic compositions for the skin as an additive, or as a principal active component in treating creams or lotions for the hands or face, or even as an additive in anti-solar cream compositions, tinting cream compositions, makeup remover milks, bubble bath formulations and the like.

Thus the present invention also relates to cosmetic compositions such as defined above, comprising at least one polymer of formula I described hereafter in Examples 1–20. Moreover, the present invention relates to a process comprising applying to the hair or the skin a cosmetic composition containing at least one polymer of formula I as defined above.

The polymers of formula I possess other interesting properties, principally, germicidal characteristics and particularly bactericidal and fungicidal characteristics. The polymers of the present invention also exhibit surface-active characteristics.

Their germicidal, surfactant or film-forming characteristics make them useful principally as preservatives, for example, in cosmetic preparations.

The following non-limiting examples illustrate the invention. Unless otherwise stated, all parts and percentages are by weight.

EXAMPLE 1

202 g (1 mole) of 1,3-dibromopropane are added to a solution of 326.6 g (1 mole) of N-dodecyl-N,N',N'-trimethyl-1,6-diamino hexane in 2 liters of methanol. The resulting reaction mixture is heated for 60 hours at reflux and then concentrated to dryness under reduced pressure. The residue is washed with ether, filtered and dried under reduced pressure in the presence of $P_2O_5$. The polymer obtained contains 29.1% of $Br^-$ and is soluble in water and ethanol.

EXAMPLE 2

215 g (1 mole) of 1,4-dibromo butane are added to a solution of 214.4 g (1 mole) of N,N-dibutyl-N,N'-dimethyl-1,3-diamino propane in 1.5 liters of methanol. The resulting reaction mixture is heated to reflux for 100 hours and then concentrated to dryness under reduced pressure. The residue is washed with ether, filtered and dried under reduced pressure in the presence of $P_2O_5$. The polymer obtained contains 30.9% $Br^-$ and is soluble in water and ethanol.

The preparation of other quaternized polymers of formula I, as well as an indication of their solubility characteristics, are set forth in the following Table. In all these examples, the method of preparation is method (a) defined above.

TABLE I

| Ex. No. | $R'_1$ | $R'_2$ | A | B | X | Soluble In |
|---|---|---|---|---|---|---|
| 3 | $C_8H_{17}$ | $CH_3$ | $(CH_2)_3$ | $(CH_2)_6$ | Br | Water and ethanol |
| 4 | $C_8H_{17}$ | $CH_3$ | $(CH_2)_3$ |  | Br | Water and ethanol |

TABLE I-continued

| Ex. No. | R'₁ | R'₂ | A | B | X | Soluble In |
|---|---|---|---|---|---|---|
| 5 | $C_8H_{17}$ | $CH_3$ | $(CH_2)_3$ | $CH_2-CH(OH)-CH_2$ | Cl | Water and ethanol |
| 6 | $C_8H_{17}$ | $CH_3$ | $(CH_2)_6$ | $(CH_2)_4$ | Br | Water and ethanol |
| 7 | $C_8H_{17}$ | $CH_3$ | $(CH_2)_{10}$ | $(CH_2)_2-O-(CH_2)_2$ | Br | Water and ethanol |
| 8 | $C_{12}H_{25}$ | $CH_3$ | $(CH_2)_3$ | $(CH_2)_6$ | Br | Water and ethanol |
| 9 | $C_{12}H_{25}$ | $CH_3$ | $(CH_2)_{10}$ | $(CH_2)_4$ | Br | Water and ethanol |
| 10 | $C_{12}H_{25}$ | $CH_3$ | $(CH_2)_{10}$ | $CH_2-CH(OH)-CH_2$ | Br | Water and ethanol |
| 11 | $C_3H_7$ | $C_3H_7$ | $(CH_2)_3$ | $(CH_2)_6$ | Br | Water and ethanol |
| 12 | $C_3H_7$ | $C_3H_7$ | $(CH_2)_3$ | $CH_2-C_6H_4-CH_2$ | Br | Water and ethanol |
| 13 | $C_3H_7$ | $C_3H_7$ | $(CH_2)_3$ | $CH_2-CH(OH)-CH_2$ | Br | Water and ethanol |
| 14 | $C_4H_9$ | $C_4H_9$ | $(CH_2)_3$ | $(CH_2)_6$ | Br | Water and ethanol |
| 15 | $C_4H_9$ | $C_4H_9$ | $(CH_2)_3$ | $CH_2-CH(OH)-CH_2$ | Cl | Water and ethanol |
| 16 | $C_8H_{17}$ | $C_8H_{17}$ | $(CH_2)_6$ | $(CH_2)_3$ | Br | Water and ethanol |
| 17 | $C_8H_{17}$ | $C_8H_{17}$ | $(CH_2)_6$ | $(CH_2)_4$ | Br | Water and ethanol |
| 18 | $C_2H_5$ | $C_2H_5$ | $(CH_2)_3$ | $CH_2-CH(OH)-CH_2$ | Cl | Water and ethanol |
| 19 | Cyclo-hexyl | $CH_3$ | $(CH_2)_3$ | $(CH_2)_4$ | Br | Water and ethanol |
| 20 | Benzyl | $CH_3$ | $(CH_2)_3$ | $(CH_2)_6$ | Br | Water and ethanol |
| 21 | $C_2H_5$ | $C_2H_5$ | $(CH_2)_3$ | $(CH_2)_4$ | Br | Water and ethanol |
| 22 | $C_2H_5$ | $C_2H_5$ | $(CH_2)_3$ | $(CH_2)_6$ | Br | Water and ethanol |
| 23 | $C_4H_9$ | $CH_3$ | $(CH_2)_3$ | $(CH_2)_4$ | Br | Water and ethanol |
| 24 | $C_3H_7$ | $CH_3$ | $(CH_2)_3$ | $(CH_2)_4$ | Br | Water and ethanol |
| 25 | $C_{16}H_{33}$ | $CH_3$ | $(CH_2)_3$ | $(CH_2)_4$ | Br | Water and ethanol |
| 26 | $C_{16}H_{33}$ | $CH_3$ | $(CH_2)_3$ | $(CH_2)_6$ | Br | Water and ethanol |
| 27 | $C_{18}H_{37}$ | $CH_3$ | $(CH_2)_3$ | $(CH_2)_6$ | Br | Water-ethanol ethanol |
| 28 | $C_{18}H_{37}$ | $CH_3$ | $(CH_2)_3$ | $(CH_2)_4$ | Br | Water-ethanol ethanol |
| 29 | $(CH_2)_2-O-(CH_2)_2$ | | $(CH_2)_3$ | $(CH_2)_6$ | Br | Water, water-ethanol |
| 30 | $(CH_2)_2-O-(CH_2)_2$ | | $(CH_2)_3$ | $(CH_2)_4$ | Br | Water, water-ethanol |
| 31 | $(CH_2)_2-O-(CH_2)_2$ | | $(CH_2)_3$ | $CH_2-CHOH-CH_2$ | Cl | Water, water-ethanol |

EXAMPLES OF COMPOSITION

EXAMPLE A

A dye shampoo composition is prepared by admixing the following components:

| | |
|---|---|
| Nonylphenol polyoxyethylenated with 4 moles of ethylene oxide | 25 g |
| Nonylphenol polyoxyethylenated | |

| | | |
|---|---|---|
| with 9 moles of ethylene oxide | 23 g | |
| Compound of Example 8 | 4 g | |
| Ethyl alcohol, 96% | 7 g | |
| Propylene glycol | 14 g | |
| Ammonia, 22° Bé | 10 ml | |
| Metadiaminoanisol sulfate | 0.030 g | |
| Resorcinol | 0.400 g | |
| Metaamino phenol base | 0.150 g | |
| Paraamino phenol base | 0.087 g | |
| Nitro paraphenylene diamine | 1.000 | |
| Ethylenediamine tetraacetic acid, sold under the mark Trilon B | 3.000 g | |
| Sodium bisulfite, d = 1.32 | 1.200 g | |
| Water, q.s.p. | 100.000 g | |

50 g of the above admixture are mixed in a bowl with the same quantity of H$_2$O$_2$ (20 volumes). The resulting mixture which is gel is then applied to the hair with a brush and is permitted to remain in contact therewith for 30 minutes. Thereafter the hair is rinsed. The thus treated hair combs easily and is soft to the touch. Subsequently the hair is set and dried and the hair thus treated is lively, shiny, has body (volume), is soft to the touch and combs easily. On brown hair, there is thus obtained a chestnut coloration.

Essentially the same results can be achieved by replacing in the above composition the compound of Example 8 by 3 grams of the compound of Example 2.

EXAMPLE B

A dye shampoo composition is prepared by admixing the following components:

| | |
|---|---|
| Nonylphenol polyoxyethylenated with 4 moles of ethylene oxide | 25 g |
| Nonylphenol polyoxyethylenated with 9 moles of ethylene oxide | 23 g |
| Compound of Example 3 | 5 g |
| Ethyl alcohol, 96% | 7 g |
| Propylene glycol | 14 g |
| Ammonia, 22° Bé | 10 ml |
| Metadiaminoanisol sulfate | 0.030 g |
| Resorcinol | 0.400 g |
| Metaamino phenol base | 0.150 g |
| Paraamino phenol base | 0.087 g |
| Nitro paraphenylene diamine | 1.000 g |
| Trilon B | 3.000 g |
| Sodium bisulfite, d = 1.32 | 1.200 g |
| Water, q.s.p. | 100.000 g |

50 g of the above admixture are mixed in a bowl with the same amount of H$_2$O$_2$ (20 volumes). The resulting mixture which is a gel is then applied to the hair with a brush and is permitted to remain in contact therewith for 30 minutes. Thereafter the hair is rinsed. The thus treated hair combs easily and is soft to the touch. Subsequently the hair is set and dried and the hair thus treated is shiny, lively, has body (volume), is soft to the touch and combs easily. On brown hair, a chestnut coloration is obtained.

Essentially the same results are achieved by replacing in the above composition the compound of Example 3 by 4 g of the compound of Example 1.

EXAMPLE C

An oxidation dye cream composition is prepared by admixing the following components:

| | |
|---|---|
| Cetyl stearyl alcohol | 22 g |
| Oleyl diethanolamide | 5 g |
| Sodium cetyl stearyl sulfate | 4 g |
| Compound of Example 12 | 6 g |
| Ammonia, 22° Bé | 12 ml |
| Metadiaminoanisol sulfate | 0.048 g |
| Resorcinol | 0.420 g |
| Metaamino phenol base | 0.150 g |
| Nitro paraphenylene diamine | 0.085 g |
| Para toluylene diamine | 0.004 g |
| Trilon B | 1.000 g |
| Sodium bisulfite, d = 1.32 | 1.200 g |
| Water, q.s.p. | 100.000 g |

30 g of this formulation are mixed with 45 g of H$_2$O$_2$ (20 volumes). The resulting mixture which is a smooth, thick, pleasant to apply cream which adheres well to the hair is then applied to the hair and is permitted to remain in contact therewith for 30 minutes. Thereafter, the hair is rinsed and dried.

On 100% white hair, a blond coloration is achieved. The thus treated hair, in the wet or dry state, is easy to comb and the dry hair has a shiny appearance and is agreeable and soft to the touch.

Essentially the same results are achieved by replacing in the above composition the compound of Example 12 by one of the following:

6 g of the compound of Example 4 or 6 g of the compound of Example 5.

EXAMPLE D

A hair treating lotion is prepared by admixing the following components:

| | |
|---|---|
| Compound of Example 9 | 5 g |
| Monoethanolamine, q.s.p. pH = 7.5 | |
| Water, q.s.p. | 100 ml |

The resulting mixture is applied to the hair and is permitted to remain in contact therewith for 5 minutes. Thereafter the hair is rinsed and the thus treated hair has a soft touch and combs easily. Subsequently, the hair is set and dried and the dried haid combs easily, is shiny, lively and has body.

Essentially the same results are obtained by replacing in the above composition the compound of Example 9 by one of the following:

4 g of the compound of Example 6 or
6 g of the compound of Example 15.

EXAMPLE E

A hair setting lotion for sensitized hair is prepared by admixing the following components:

| | |
|---|---|
| Polyvinylpyrrolidone | 1.5 g |
| Compound of Example 7 | 2.5 g |
| Ethyl alcohol, q.s.p. | 100 ml |

The resulting mixture is applied to the hair which is then set and dried. The dried hair, which is hard and plasticized, is shiny, has volume, is soft to the touch and combs easily.

Essentially the same results are achieved by replacing in the above composition the compound of Example 7 by 2 g of the compound of Example 14.

EXAMPLE F

A hair restructuring lotion which is employed with a subsequent rinsing operation is prepared by admixing the following components:

2 g of dimethylol ethylene thiourea are mixed with 25 ml of a solution containing:

| | |
|---|---|
| Compound of Example 10 | 5 g |
| HCl, q.s.p. pH = 2.5 | |
| Water, q.s.p. | 100 ml |

The resulting mixture is then applied to washed and dried hair and is permitted to remain in contact therewith for 10 minutes. Thereafter, the hair is rinsed. The thus treated hair combs easily and has a soft touch. The hair is then set and dried under a hood. The dry hair combs easily, is shiny, lively and has body (volume).

Essentially the same results are achieved by replacing in the above composition the compound of Example 10 by one of the following:
4 g of the compound of Example 11 or
4.5 g of the compound of Example 13.

EXAMPLE G

A hair restructuring lotion which can be employed without a subsequent rinsing operation is prepared by admixing the following components:

0.3 g of dimethylol ethylene thiourea is mixed with 25 ml of the following solution:

| | |
|---|---|
| Compound of Example 16 | 0.5 g |
| Phosphoric acid, q.s.p. pH = 2.8 | |
| Water, q.s.p. | 100 ml |

The resulting mixture is applied to washed and dried hair before setting it. The thus treated hair combs easily and is soft to the touch. The hair is then set and dried and the dried hair is shiny, lively, has body (volume), is soft to the touch and combs easily.

Essentially the same results are obtained by replacing in the above composition the compound of Example 16 by 0.6 g of the compound of Example 17.

EXAMPLE H

A dye shampoo is prepared by admixing the following components:

| | |
|---|---|
| Nonylphenol polyoxyethylenated with 4 moles of ethylene oxide | 25 g |
| Nonylphenol polyoxyethylenated with 9 moles of ethylene oxide | 23 g |
| Compound of Example 22 | 4 g |
| Ethyl alcohol, 96% | 7 g |
| Propylene glycol | 14 g |
| Ammonia, 22° Bé | 10 ml |
| Metadiaminoanisole sulfate | 0.030 g |
| Resorcinol | 0.400 g |
| Metaamino phenol base | 0.150 g |
| Paraamino phenol base | 0.087 g |
| Nitro paraphenylene diamine | 1.000 g |
| Trilon B | 3.000 g |
| Sodium bisulfite, d = 1.32 | 1.200 g |
| Water, q.s.p. | 100.000 g |

50 g of the above formulation are mixed in a bowl with the same quantity of $H_2O_2$ (20 volumes). The resulting mixture which is a gel is then applied to the hair with a brush and is permitted to remain in contact therewith for 30 minutes. Thereafter the hair is rinsed and the thus treated hair combs easily and is soft to the touch. The hair is then set and dried and the dried hair is shiny, lively, has body (volume), is soft to the touch and combs easily. On brown hair, a chestnut coloration is obtained.

Essentially the same results are achieved by replacing in the above composition the compound of Example 22 by 3 g of the compound of any one of Examples 23, 24, 30 and 31.

EXAMPLE I

An oxidation dye cream composition is prepared by admixing the following components:

| | |
|---|---|
| Cetyl stearyl alcohol | 22 g |
| Oleyl diethanolamide | 5 g |
| Sodium cetyl stearyl sulfate | 4 g |
| Compound of Example 29 | 6 g |
| Ammonia, 22° Bé | 12 ml |
| Metadiaminoanisole sulfate | 0.048 g |
| Resorcinol | 0.420 g |
| Metaamino phenol base | 0.150 g |
| Nitro paraphenylene diamine | 0.085 g |
| Para toluylene diamine | 0.004 g |
| Trilon B | 1.000 g |
| Sodium bisulfite, d = 1.32 | 1.200 g |
| Water, q.s.p. | 100.000 g |

30 g of this formulation are mixed with 45 g of $H_2O_2$ (20 volumes). The resulting mixture which is a smooth, thick, pleasant to apply cream which adheres well to the hair, is then applied to the hair and is permitted to remain in contact therewith for 30 minutes. Thereafter the hair is rinsed and dried. On 100% white hair, a blond coloration is obtained. The thus treated hair is easy to comb in both the wet and dry states and the dry hair has a shiny appearance and is pleasant and soft to the touch.

Essentially the same results are achieved by replacing in the above composition the compound of Example 29 by one of the following:
6 g of the compound of Example 21 or 22.

EXAMPLE J

A hair setting lotion for sensitized hair is prepared by admixing the following components:

| | |
|---|---|
| Polyvinylpyrrolidone | 1.5 g |
| Compound of Example 24 | 2.5 g |
| Ethyl alcohol, q.s.p. | 100 ml |

The resulting mixture is applied to hair which is then set and dried. The hair thus treated, which is hard and plasticized, is shiny, has volume, is soft to the touch and combs easily.

Essentially the same results are achieved by replacing in the above composition the compound of Example 24 by 2 g of the compound of Example 21.

EXAMPLE K

A hair restructuring lotion which is employed with a subsequent rinsing operation is prepared by admixing the following components:

2 g of dimethylol ethylene thiourea are mixed with 25 ml of a solution containing:

| The compound of Example 27 | 5 g |
|---|---|
| HCl, q.s.p. pH = 2.5 | |
| Water, q.s.p. | 100 ml. |

The resulting mixture is then applied to washed and dried hair and is permitted to remain in contact therewith for 10 minutes. Thereafter the hair is rinsed. The thus treated hair combs easily and has a soft touch. The hair is then set and dried under a hood. The dry hair combs easily, is shiny, lively and has body (volume).

Essentially the same results are obtained by replacing in the above composition the compound of Example 27 by one of the following:
4 g of the compound of Example 22 or
4.5 g of the compound of Example 28.

EXAMPLE L

A hair restructuring lotion which can be employed without a subsequent rinsing operation is prepared by admixing the following components:

0.3 g of dimethylol ethylene thiourea is mixed with 25 ml of the following solution:

| The compound of Example 25 | 0.5 g |
|---|---|
| Phosphoric acid, q.s.p. pH = 2.8 | |
| Water, q.s.p. | 100 ml |

The resulting mixture is then applied to washed and dried hair before setting it. The thus treated hair combs easily and is soft to the touch. The hair is then set and dried and the dried hair is shiny, lively, has body (volume), is soft to the tough, and combs easily.

Essentially the same results are obtained by replacing in the above composition the compound of Example 25 by 0.6 g of the compound of Example 26.

EXAMPLE M

A pre-shampoo composition is prepared by admixing the following components:

| Compound of Example 22 | 2 g |
|---|---|
| Monoethanolamine, q.s.p. pH = 7 | |
| Water, q.s.p. | 100 cc |

10 g of this composition are applied to soiled, dry hair. The composition is permitted to remain in contact with the hair for 2 minutes. Thereafter the hair is shampooed with a conventional anionic shampoo formulation.

EXAMPLE N

A pre-shampoo composition is prepared by admixing the following components:

| Compound of Example 22 | 2 g |
|---|---|
| Monoethanolamine, q.s.p. pH = 7 | |
| Water, q.s.p. | 100 g |

10 g of the above composition are applied to soiled, dry hair. The composition is permitted to remain in contact with the hair for 2 minutes. Thereafter the hair is shampooed with a conventional anionic shampoo formulation. The thus treated hair combs easily and has a soft touch, in the wet state as well as after drying.

Essentially analogous results are obtained by replacing in the above composition the compound of Example 22 by the compounds of Examples 25 to 31.

Comparable pre-shampooing compositions have been prepared in the form of aerosols with the same polymers. Typically such an aerosol composition can be prepared by admixing the following components:

| Compound of Example 22 | 8 g |
|---|---|
| Monoethanolamine, q.s.p. pH = 7 | |
| Water, q.s.p. | 100 g |

25 g of this mixture are introduced into an aerosol container. Then sufficient nitrogen is introduced into the container so as to establish therein a pressure of 5 kg/cm$^2$.

Using the resulting aerosol formulation, the dry hair to be washed is impregnated therewith and the thus sprayed formulation is permitted to remain in contact with the hair for a few minutes. Thereafter the thus treated hair is shampooed with a conventional anionic shampoo formulation.

EXAMPLE O

A two-part permanent waving composition is prepared by admixing the following components:

| Part A - Reducing composition for the first stage of a permanent waving operation. | |
|---|---|
| Thioglycolic acid | 8 g |
| Ammonia, sufficient for pH = 7 | |
| Ammonium bicarbonate | 6.4 g |
| Dimethyl distearyl ammonium chloride | 0.2 g |
| Polymer of Example 22 | 4 g |
| Oleyl alcohol oxyethylenated with 20 moles of ethylene oxide | 1 g |
| Perfume, sufficient amount | |
| water, sufficient for | 100 g |
| Part B - Fixing agent for the second stage of the permanent waving operation | |
| Dimethyl distearyl ammonium chloride | 0.3 g |
| Phenacetin | 0.1 g |
| Citric acid | 0.3 g |
| Nonylphenol oxyethylenated with 9 moles of ethylene oxide | 1 g |
| H$_2$O$_2$, sufficient amount, 8 vol. | |
| Dye, sufficient amount | |
| Perfume, sufficient amount | |
| Water, sufficient for | 100 g |

Part A is applied to the hair rolled on curlers and is permitted to remain in contact therewith for a period of about 5 to 15 minutes. Thereafter, the hair is rinsed with water.

Part B is then applied to the hair and is permitted to remain in contact therewith for 10 minutes, after which the hair is rinsed. The hair is then set and dried.

The hair thus treated, when wet, is easily combed and is soft to the touch. Further, the hair thus treated, when dry is shiny and lively and is easily combed.

What is claimed is:

1. A hair dye composition comprising a cream or gel a carrier a quaternized polymer having recurring units of the formula

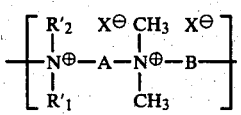

wherein
- $X^{\ominus}$ represents an anion derived from an organic or mineral acid,
- $R'_2$ is an aliphatic radical having a maximum of 20 carbon atoms,
- $R'_1$ is alkyl having 2-20 carbon atoms, cycloalkyl having 5 or 6 carbon atoms or phenylalkyl wherein the alkyl moiety has 1-3 carbon atoms, or $R'_1$ and $R'_2$ together represent a polymethylene radical having 4 or 5 carbon atoms or $-(CH_2)_2-O-(CH_2)_2-$,
- A represents a divalent group of the formula

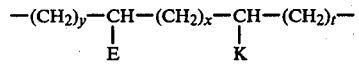

wherein x, y and t are whole numbers ranging from 0 to 11 and being such that the sum $(x+y+t)$ is greater than or equal to 0 and less than 18, and E and K represent hydrogen, B represents a divalent group of the formula

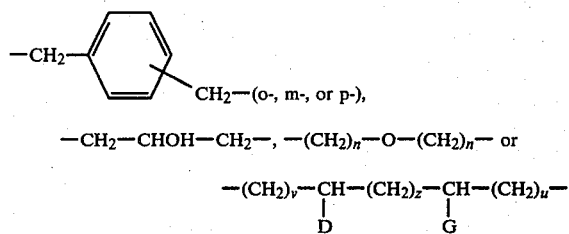

$-CH_2-CHOH-CH_2-$, $-(CH_2)_n-O-(CH_2)_n-$ or $$-(CH_2)_v-\underset{D}{CH}-(CH_2)_z-\underset{G}{CH}-(CH_2)_u-$$

wherein D and G represent hydrogen and v, z and u are whole numbers ranging from 0 to 11, two of them being able to be simultaneously equal to 0 such that the sum $(v+z+u)$ is greater than or equal to 1 and lower than 18, and such that the sum $(v+z+u)$ is greater than 1 when the sum $(x+y+t)$ is equal to 0, and n is a whole number equal to 2 or 3, said polymer being present in an amount between 0.25 and 10 weight percent of said composition, and an effective amount of hair dye to color the hair.

2. The hair dye composition of claim 1 wherein
X represents a halide,
$R'_1$ represents an alkyl containing 2-20 carbon atoms, cycloalkyl having 5 or 6 carbon atoms or phenylalkyl wherein the alkyl moiety has 1-3 carbon atoms; E, K, D and G represent hydrogen; v, z and u represent a number ranging from 1 to 5, two of them being able to be equal to 0; x, y and t represent numbers ranging from 0 to 5; and
$R'_2$ is alkyl having 1-20 carbon atoms; or $R'_1$ and $R'_2$ together represent $-(CH_2)_2-O-(CH_2)_2-$.

3. The hair dye composition of claim 1 wherein
$R'_1$ is alkyl having 2-18 carbon atoms;
$R'_2$ is alkyl having from 1 to 8 carbon atoms; or $R'_1$ and $R'_2$ together represent $-(CH_2)_2-O-(CH_2)_2-$,
A is polymethylene having 2 to 12 carbon atoms or polymethylene having 2 to 12 carbon atoms and branched by one or two alkyl substituents having 1 to 12 carbon atoms,
B is xylylidene, polymethylene having 3 to 10 carbon atoms or polymethylene having 3 to 10 carbon atoms and branched by one or two alkyl substituents having 1 to 12 carbon atoms, and
X is chloride or bromide.

4. The hair dye composition of claim 1 wherein $R'_1$, $R'_2$, A, B and X are selected from the combinations consisting of
(1) $R'_1$ is $C_{12}H_{25}$, $R'_2$ is $CH_3$, A is $(CH_2)_6$, B is $(CH_2)_3$ and X is Br;
(2) $R'_1$ is $C_4H_9$, $R'_2$ is $C_4H_9$, A is $(CH_2)_3$, B is $(CH_2)_4$ and X is Br;
(3) $R'_1$ is $C_8H_{17}$, $R'_2$ is $CH_3$, A is $(CH_2)_3$, B is $(CH_2)_6$ and X is Br;
(4) $R'_1$ is $C_8H_{17}$, $R'_2$ is $CH_3$, A is $(CH_2)_3$, B is p-xylylene and X is Br;
(5) $R'_1$ is $C_8H_{17}$, $R'_2$ is $CH_3$, A is $(CH_2)_3$, B is $-CH_2-CHOH-CH_2-$ and X is Cl;
(6) $R'_1$ is $C_8H_{17}$, $R'_2$ is $CH_3$, A is $(CH_2)_6$, B is $(CH_2)_4$ and X is Br;
(7) $R'_1$ is $C_8H_{17}$, $R'_2$ is $CH_3$, A is $(CH_2)_{10}$, B is $(CH_2)_2-O-(CH_2)_2$ and X is Br;
(8) $R'_1$ is $C_{12}H_{25}$, $R'_2$ is $CH_3$, A is $(CH_2)_3$, B is $(CH_2)_6$ and X is Br;
(9) $R'_1$ is $C_{12}H_{25}$, $R'_2$ is $CH_3$, A is $(CH_2)_{10}$, B is $(CH_2)_4$ and X is Br;
(10) $R'_1$ is $C_{12}H_{25}$, $R'_2$ is $CH_3$, A is $(CH_2)_{10}$, B is $-CH_2CHOH-CH_2-$ and X is Br;
(11) $R'_1$ is $C_3H_7$, $R'_2$ is $C_3H_7$, A is $(CH_2)_3$, B is $(CH_2)_6$ and X is Br;
(12) $R'_1$ is $C_3H_7$, $R'_2$ is $C_3H_7$, A is $(CH_2)_3$, B is p-xylylene and X is Br;
(13) $R'_1$ is $C_3H_7$, $R'_2$ is $C_3H_7$, A is $(CH_2)_3$, B is $-CH_2CHOHCH_2-$ and X is Br;
(14) $R'_1$ is $C_4H_9$, $R'_2$ is $C_4H_9$, A is $(CH_2)_3$, B is $(CH_2)_6$ and X is Br;
(15) $R'_1$ is $C_4H_9$, $R'_2$ is $C_4H_9$, A is $(CH_2)_3$, B is $CH_2CHOHCH_2-$ and X is Cl;
(16) $R'_1$ is $C_8H_{17}$, $R'_2$ is $C_8H_{17}$, A is $(CH_2)_6$, B is $(CH_2)_3$ and X is Br;
(17) $R'_1$ is $C_8H_{17}$, $R'_2$ is $C_8H_{17}$, A is $(CH_2)_6$, B is $(CH_2)_4$ and X is Br;
(18) $R'_1$ is $C_2H_5$, $R'_2$ is $C_2H_5$, A is $(C_2)_3$, B is $-CH_2CHOHCH_2-$ and X is Cl;
(19) $R'_1$ is cyclohexyl, $R'_2$ is $CH_3$, A is $(CH_2)_3$, B is $(CH_2)_4$ and X is Br;
(20) $R'_1$ is benzyl, $R'_2$ is $CH_3$, A is $(CH_2)_3$, B is $(CH_2)_6$ and X is Br;
(21) $R'_1$ is $C_2H_5$, $R'_2$ is $C_2H_5$, A is $(CH_2)_3$, B is $(CH_2)_4$ and X is Br;
(22) $R'_1$ is $C_2H_5$, $R'_2$ is $C_2H_5$, A is $(CH_2)_3$, B is $(CH_2)_6$ and X is Br;
(23) $R'_1$ is $C_4H_9$, $R'_2$ is $CH_3$, A is $(CH_2)_3$, B is $(CH_2)_4$ and X is Br;
(24) $R'_1$ is $C_3H_7$, $R'_2$ is $CH_3$, A is $(CH_2)_3$, B is $(CH_2)_4$ and X is Br;
(25) $R'_1$ is $C_{16}H_{33}$, $R'_2$ is $CH_3$, A is $(CH_2)_3$, B is $(CH_2)_4$ and X is Br;
(26) $R'_1$ is $C_{26}H_{33}$, $R'_2$ is $CH_3$, A is $(CH_2)_3$, B is $(CH_2)_6$ and X is Br;
(27) $R'_1$ is $C_{18}H_{37}$, $R'_2$ is $CH_3$, A is $(CH_2)_3$, B is $(CH_2)_6$ and X is Br;
(28) $R'_1$ is $C_{18}H_{37}$, $R'_2$ is $CH_3$, A is $(CH_2)_3$, B is $(CH_2)_4$ and X is Br;
(29) $R'_1$ and $R'_2$ together form $(CH_2)_2-O-(CH_2)_2$, A is $(CH_2)_3$, B is $(CH_2)_6$ and X is Br;

(30) $R'_1$ and $R'_2$ together form $(CH_2)_2$—O—$(CH_2)_2$, A is $(CH_2)_3$, B is $(CH_2)_4$ and X is Br; and

(31) $R'_1$ and $R'_2$ together form $(CH_2)_2$—O—$(CH_2)_2$, A is $(CH_2)_3$, B is —$CH_2$—CHOH—$CH_2$— and X is Cl.

5. The hair dye composition of claim 1 wherein said vehicle is a cream.

6. The hair dye composition of claim 5 wherein said cream comprises a soap of a $C_{12}$ to $C_{20}$ fatty acid and an alkalizing agent.

7. The hair dye composition of claim 5 wherein said cream comprises a natural or synthetic alcohol having between 12 and 20 carbon atoms in admixture with an emulsifier.

8. The hair dye composition of claim 36 wherein said cream also includes an effective amount of a fatty amide.

9. The hair dye composition of claim 1 wherein said hair dye is a direct hair dye.

10. The hair dye composition of claim 1 wherein said hair dye is an oxidation hair dye.

11. The hair dye composition of claim 1 which also includes, as an oxyethylenated non-ionic compound, selected from the group consisting of oleyl alcohol having 4 moles of ethylene oxide, oleylalcohol having 10 moles of ethylene oxide, a $C_{10}$–$C_{12}$ synthetic fatty alcohol having 4 moles of ethylene oxide, a $C_{10}$–$C_{12}$ synthetic fatty alcohol having 6 moles of ethylene oxide, a $C_9$–$C_{15}$ synthetic fatty alcohol having 2 moles of ethylene oxide, a $C_9$–$C_{15}$ synthetic fatty alcohol having 6 moles of ethylene oxide, a $C_9$–$C_{15}$ synthetic fatty alcohol having 9 moles of ethylene oxide, nonylphenol polyether having 4 moles of ethylene oxide and nonylphenol polyether having 9 moles of ethylene oxide, said oxyethylenated non-ionic compound being present in an amount ranging from 5 to 60 weight percent of said composition and, as a solvent, a lower aliphatic alcohol or a glycol present in an amount ranging from 2 to 20 percent by weight of said composition.

12. The hair dye composition of claim 1 which also includes, as a polyglycerolated non-ionic compound, selected from the group consisting of oleyl alcohol having 2 moles of glycerol and oleyl alcohol having 4 moles of glycerol, said polyglycerolated non-ionic compound being present in an amount ranging from 5 to 60 weight percent of said composition and, as a solvent, a lower aliphatic alcohol or a glycol present in an amount ranging from 2 to 20 percent by weight of said composition.

13. The hair dye composition of claim 11 or 12 which also includes, as an alkaline alkyl sulfate or an oxyethylenated alkaline alkyl sulfate, selected from the group consisting of sodium lauryl sulfate, ammonium lauryl sulfate, triethanolamine lauryl sulfate, monoethanolamine lauryl sulfate, sodium laurylether sulfate oxyethylenated with 2.2 moles of ethylene oxide and monoethanolamine laurylether sulfate oxyethylenated with 2.2 moles of ethylene oxide, present in an amount ranging from 0.5 to 15 percent by weight of said composition.

14. The hair dye composition of claim 11 or 12 which also includes a fatty amide.

15. The hair dye composition of claim 11 or 12 which also includes a natural or synthetic fatty alcohol.

16. The hair dye composition of claim 11 or 12 admixed with hydrogen peroxide.

17. A process for dyeing hair comprising applying thereto the hair dye composition of claim 1, permitting said composition to remain in contact with the hair for a time sufficient to obtain the desired dyeing effect and thereafter rinsing the hair.

* * * * *